US00PP12219P2

(12) United States Plant Patent
Torres

(10) Patent No.: US PP12,219 P2
(45) Date of Patent: Nov. 27, 2001

(54) APPLE TREE NAMED 'TRIPLE E' FUJI

(76) Inventor: Octavano C. Torres, 8300 Russell Rd., Mesa, WA (US) 99343

( * ) Notice: Subject to any disclaimer, the term of this patent is extended or adjusted under 35 U.S.C. 154(b) by 0 days.

(21) Appl. No.: 09/392,985

(22) Filed: Sep. 9, 1999

(51) Int. Cl.[7] ..... A01H 5/00
(52) U.S. Cl. ..... Plt./168

(58) Field of Search ..... Plt./168

*Primary Examiner*—Bruce R. Campell
*Assistant Examiner*—Susan B. McCormick
(74) *Attorney, Agent, or Firm*—Klarquist Sparkman, LLP

(57) ABSTRACT

A new and distinct variety of apple tree named 'Triple E' Fuji characterized by a fruit almost solid red in color, with no striping, which matures earlier than the 'BC2' Fuji variety.

2 Drawing Sheets

BACKGROUND OF THE INVENTION

The present invention comprises a new and distinct variety of apple tree 9 (*Malus pumila*), referred to by the varietal name 'Triple E' Fuji.

My new variety of tree was discovered in an orchard in Mesa, Wash., USA, growing among trees of the Fuji variety 'BC2' trees grafted onto 'M106' apple rootstock. 'M106' and 'BC2' are both believed to be unpatented. Second generation trees of my new variety were obtained by grafting onto 'M106' apple tree rootstock. Trees of the new variety were compared to trees of the Fuji 'BC2' variety of similar age.

The new variety was observed in Mesa, Wash., to bloom at the same time as 'BC2,' however the fruit from trees of my new variety ripened in Mesa, Wash., approximately 10–14 days earlier than 'BC2.' The fruit of my new variety is distinct because of its ripening time and because it is almost entirely red (RHS 53B) in color, typically with 85–100% blush and no striping at time of ripening.

As a specific comparison, in Mesa, Wash., the fruit from trees of my new variety was ripe on Oct. 7, 1998, with 14 to 15 degrees brix. In the same field, 'BC2' fruit was ripe October 18 to October 22 at 14 to 15 degrees brix. On August 7, in this case, the 'Triple E' Fuji fruit were green. By August 21, the 'Triple E' Fuji fruit had about a 15 percent red blush, the fruit pressure was about 23 pounds, and the brix was less than 10 degrees. On September 7, the fruit of my new variety was about 40 percent red blush, about 8 degrees brix, and 20 to 22 pounds pressure. This information confirms the late maturity of fruit of my new variety in comparison to early Fuji varieties, such as 'HEISEI' Fuji (believed unpatented) and the earlier maturity of fruit of my new variety than 'BC2.' 'HEISEI' fruit have been observed to have an average color at picking time of about 50 to 60 percent red blush (14 degrees brix) and harvest over one month earlier than 'BC2.'

This invention has not been observed under all possible environmental conditions. However, the following combination of traits has been repeatedly observed in asexually-propagated progeny and is determined to comprise the new characteristics of this invention. These characteristics, in combination, distinguish 'Triple E' Fuji as a new and distinct variety of apple tree: (1) the fruit is typically 85–100 percent red when ripe; (2) the fruit matures 10–14 days before the 'BC2' variety; and (3) the fruit exhibits no striping.

Asexual reproduction by grafting onto 'M106' understock in Mesa, Wash., shows that these characteristics are established and transmitted through succeeding asexual propagations.

BRIEF DESCRIPTION OF THE PHOTOGRAPHS

Figure 1:
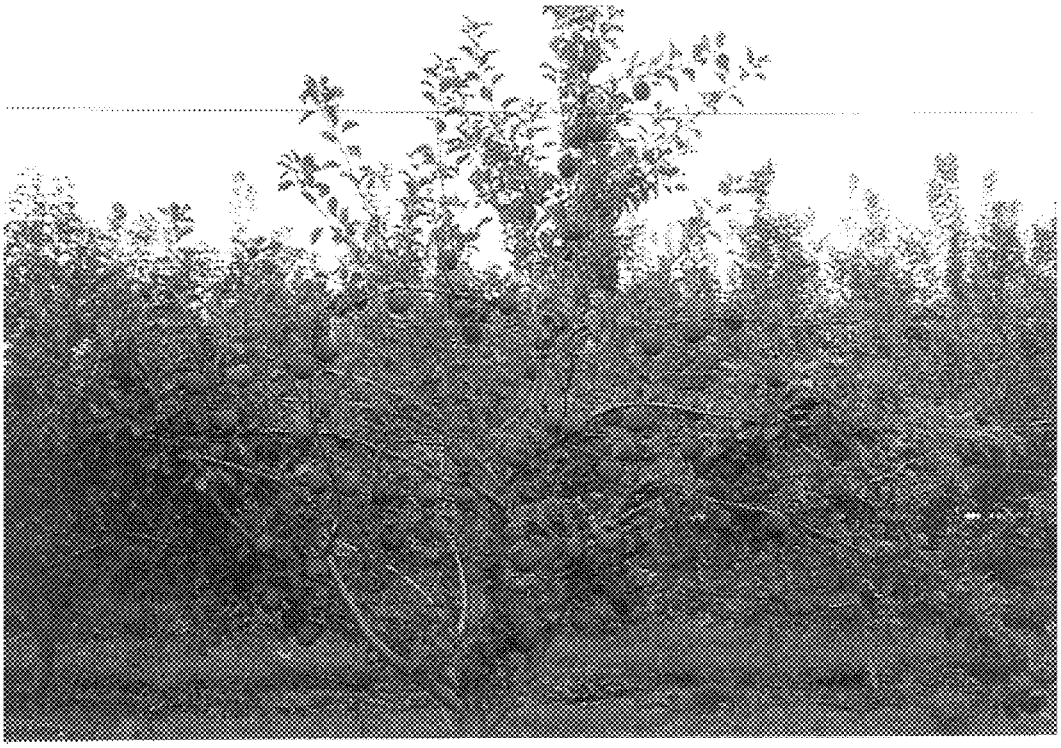
FIG. 1 is a view of an entire 'Triple E' Fuji tree laden with fruit.
Figure 2:
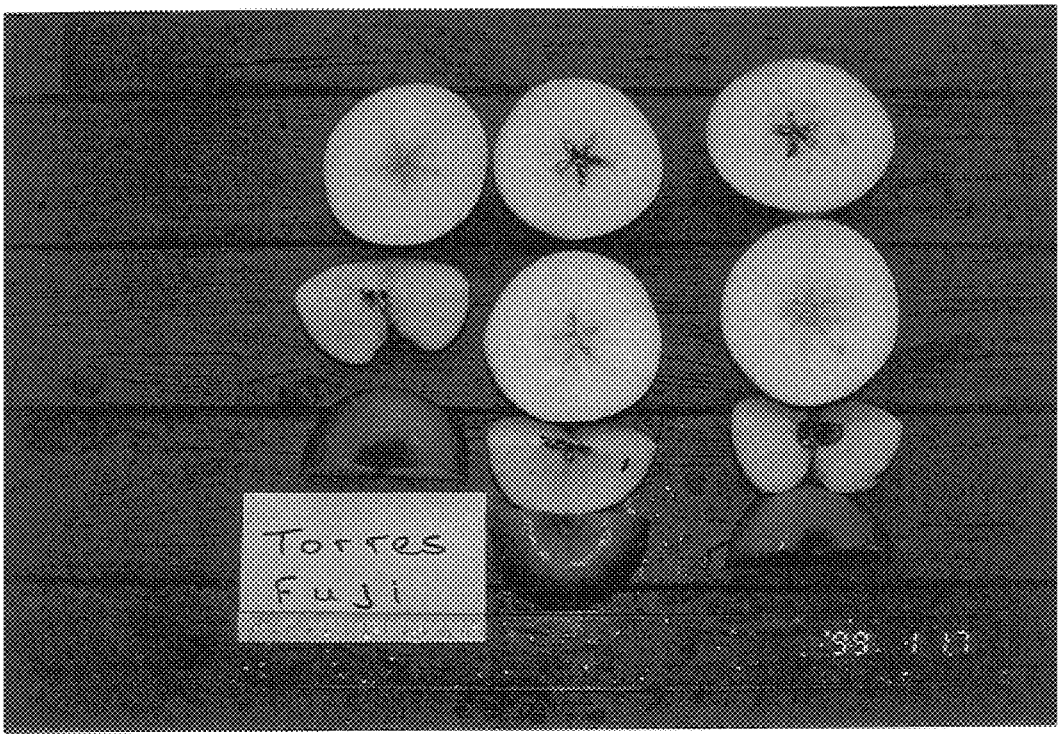
FIG. 2 is a view of the fruit of 'Triple E' Fuji. The fruit is shown sectioned through the core in two perpendicular planes, showing the seeds, flesh and outer skin.
Figure 3:
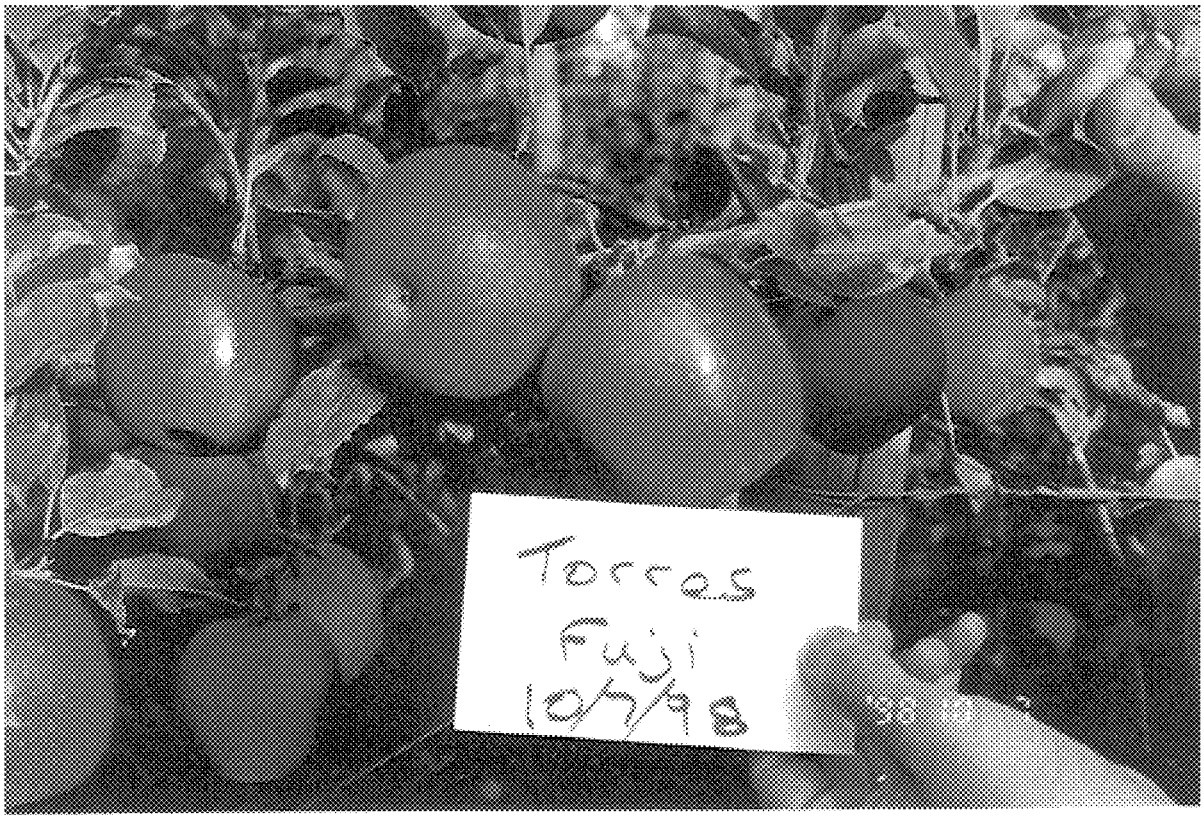
FIG. 3 is a view of the entire fruit of 'Triple E' Fuji shown still attached to the tree.

FIGS. 2 and 3 picture a card with the statement "Torres Fuji". This label identifies the breeder and applicant, Octavano Torres, not the name of the variety ('Triple E' Fuji).

DETAILED DESCRIPTION

The following is a detailed description of the invention based on plants four years of age grown under orchard practices at Mesa, Wash., USA. All trees were grafted on 'M106' apple tree rootstock.

Color references are made to The Royal Horticultural Society (R.H.S.) Colour Chart, except where the context indicates a term having its ordinary dictionary meaning. It should be noted that color may vary with factors such as growing conditions, time of year, and lighting conditions.

All trees of my new variety, insofar as I have been able to observe them, are identical in all the characteristics described below.

Species: *Malus pumila.*
Parentage: Believed a mutation of Fuji cv. 'BC2.'
Tree:

*Date of fruit maturity.*—Approximately 10–14 days before 'BC2.' In Mesa, Wash. the date of fruit maturity is usually around Oct. 7, 1998, compared to Oct. 18–22, 1998, for 'BC2' growing at the same location.

*Vigor.*—Similar to other Fuji varieties.

*Habit.*—Standard tree type with spreading branches.

Lenticels: Rounded on one-year mature wood and flatten as wood ages. Elongated in direction transverse to longitudinal axis. Lenticels on 3 year-old wood are close, between about 0.3 mm and 1 mm apart, white (RHS 155A), and of various shapes from round to oval, the oval shape being extended in a horizontal direction. Very small, typically 0.5 mm or less.

*Height.*—About 12 feet.

*Diameter.*—About 5 feet.

Branches: Young branches are pubescent. Mature, one-year-old wood has greyed purple bark (RHS 183B). Average internode length is about 11 to 20 mm Average branch size of 3 year-old wood is approximately 3.2 cm in diameter. The branch length of new growth varies from about 150 mm to 450 mm per year. The tree growth is considered medium to high vigor as compared to other apple varieties. The texture of the bark on young branches is smooth with some very light checking. The crotch angles of trees of observed trees are large, narrower if untrellised.

Trunk: Three-year-old bark on trunk has bark which is greyed purple (RHS 183D). The trunk diameter is about 8.9 cm at a height of 6 inches above soil level. The texture of the bark on the trunk of the observed trees is smooth with some checking.

Leaves:

*Shape.*—Whole leaf is ovate in shape with an acuminate apex and obtuse base.

*Size.*—Typical leaf is about 8.4 cm in length and 3.2 cm wide at the widest point.

*Color.*—Upper side: Green (RHS 138A). Underside: Green (RHS 138A).

*Margin.*—Serrate.

*Texture.*—Smooth to slightly rugose.

*Venation.*—Parallel from main vein.

*Petiole.*—Yellow green (RHS 145A) in color, about 25 mm long and about 1 mm in diameter.

*Stipules.*—Two stipules, each one about 15 mm long and about 1 mm wide.

*Arrangement.*—Alternate.

Flower:

*Flower buds.*—Ovoid in shape, about 10 mm long and 5 mm in diameter. About 4 to 7 perfect flowers per bud.

*Petals.*—Each petal is light pink (RHS 58C) to white (RHS 155D) in color. Petals average about 20 mm long and 14 mm wide at the widest point (about 10 mm wide at both the apex and base). About 5 petals per flower. Petal texture is smooth. Petals do not overlap at full bloom.

*Sepals.*—Numbering about 5 per flower. Triangular shaped, about 7 mm long, about 5 mm wide at the base, and about 0.5 mm wide at the apex. Color is yellow-green (RHS 145B). Ovary is superior to the attachments of the floral parts.

*Peduncle.*—About 17 mm long.

*Season of blooming.*—Mid-season (April 8–15 in Mesa, Wash., sometimes varying by two weeks), at approximately the same time as 'BC2' and GALA varieties in this area.

*Bloom diameter.*—35–38 mm.

*Color of closed bloom.*—Light pink (RHS 58C) to white (RHS 155C).

*Fragrance.*—No significant fragrance observed.

*Anthers.*—14 to 19 in number, yellow-green (RHS 154D) in color. Anther length is about 2.5 mm and anther filament length is about 7 mm.

*Pollen.*—Orange-yellow (RHS 162A) in color.

*Stigma below anther.*—5 per flower.

*Style.*—Light green (RHS 130D).

Fruit: Observations from six typical apples grown in 1988 in Mesa, Wash.

*Shape.*—Nearly round.

*Size.*—About 8.5 to 9.5 cm in diameter, averaging about 8.9 cm in diameter.

*Shape.*—Nearly round, some variation.

*Weight.*—Variable, averaging about 340 g.

*Stem cavity.*—Variable, 15 to 22 mm in depth, averaging about 19.5 mm in depth.

*Basin.*—Variable, shallower than stem cavity and comparable in diameter at widest part.

*Calyx.*—9 to 15 mm in depth, averaging about 11.8 mm. Sometimes open.

*Carpels.*—Variable, typically five. About 1–2 seeds per carpel, but variable. Common to have about 13 seeds per fruit.

*Ground color.*—Red (RHS 53B). When shaded, for example by a closely adjacent leaf or branch, the color is more of a yellow green (RHS 154C), which tends to become more yellow during cold storage. Typically, little or no russeting, though some russeting has been observed.

*Fruit lenticels.*—Round, non-pronounced, and yellow-white in color.

*Color markings/overcolor.*—Virtually none — almost solid ground color.

*Skin.*—Average thickness, non-greasy.

*Flesh.*—Color: Cream (RHS 158D) to white (RHS 155D). Sugar content: Typically up to 16–17 percent when ripe in Mesa, Wash. Aroma: little aroma. Texture: Firm and crispy. Flavor: sweet.

*Seed.*—Red-brown (RHS 166A to RHS 166B) in color, oval in shape, and about 6 mm long, and about 4 mm in diameter.

*Stem.*—When mature, typically greyed-red brown (like RHS 179A), about 15 mm long, and about 1 to 2 mm in diameter, with a knob at the top end.

*Pollination requirements.*—Will pollinate with any mid-season diploid variety. Diploid and not self-fertile. Not compatible with any very early or very late blooming apple varieties.

*Market use of fruit.*—The fruit is good for fresh eating and has excellent storage capacity, which result in fruit that is firm, crispy, and sweet.

*Storage.*—The fruit can be stored 9 to 12 months in controlled atmosphere storage.

*Bearing.*—Trees grown on M106 rootstock (believed to be unpatented) in Eastern Washington take about 1 to 2 years to bear fruit and about 3 years to reach production quantities. Can be biannual in bearing.

*Productivity.*—Variable, produces 40 to 50 bins of fruit, 800 to 900 pounds of fruit per bin, per acre on an annual basis when farmed correctly. The percent of packed fruit rated Washington Extra Fancy is usually double that of 'BC2' from the same location due to superior fruit coloration.

Hardiness: Cold hardy. Range of cold hardiness zones not known.

Pest/disease/resistance: Can show watercore, storage scald, and is susceptible to fireblight.

I claim:

1. A new and distinct variety of apple tree substantially as herein shown and described.

* * * * *